(12) United States Patent
Nashimoto et al.

(10) Patent No.: US 7,294,154 B2
(45) Date of Patent: Nov. 13, 2007

(54) MICROORGANISM STAINING AGENT AND USE THEREOF

(75) Inventors: Koji Nashimoto, Chiba (JP); Kazuya Ishida, Narita (JP); Yasuo Ikeda, Narashino (JP); Yoshiaki Hanaoka, Yotsukaido (JP)

(73) Assignee: Hisamitsu Pharmaceutical Co., Inc., Tosu-shi (JP)

( * ) Notice: Subject to any disclaimer, the term of this patent is extended or adjusted under 35 U.S.C. 154(b) by 0 days.

(21) Appl. No.: 10/554,285

(22) PCT Filed: Apr. 8, 2004

(86) PCT No.: PCT/JP2004/005085

§ 371 (c)(1),
(2), (4) Date: Oct. 25, 2005

(87) PCT Pub. No.: WO2004/097037

PCT Pub. Date: Nov. 11, 2004

(65) Prior Publication Data

US 2006/0263843 A1    Nov. 23, 2006

(30) Foreign Application Priority Data

Apr. 25, 2003   (JP) .............................. 2003-121701

(51) Int. Cl.
*D06P 1/00*   (2006.01)
*D06P 1/12*   (2006.01)
*C09B 23/14*  (2006.01)

(52) U.S. Cl. ................................. 8/636; 8/664; 8/657

(58) Field of Classification Search ..................... None
See application file for complete search history.

(56) References Cited

U.S. PATENT DOCUMENTS 4,853,210 A * 8/1989 Kass ........................ 435/40.51
4,940,834 A * 7/1990 Hurley et al. ............... 800/298
5,741,662 A * 4/1998 Madsen et al. ................ 435/34
2003/0171556 A1* 9/2003 Chae et al. ............ 530/388.26

FOREIGN PATENT DOCUMENTS

| JP | 48-076592 | 10/1973 |
| JP | 7-110328 | 4/1995 |
| JP | 2003-052392 | 2/2003 |

OTHER PUBLICATIONS

Ostle et al. Nile Blue a as a Fluorescent Stain for Poly-Beta-Hydroxybutyrate; Applied and Environmental Microbiology, vol. 44, No. 1 (1982) pp. 238-241.*
Yamaguchi et al. "Report of the Standardization Committee of the Japanese Society for Medical Mycology", Jpn. J. Med. Mycol., vol. 36, pp. 61-86, with English abstract and partial English translation 1995.
Medical Technology, vol. 23, No. 7, Jun. 1995, 3 pages.
"Nyo Chinsakensa No Susumekata" (Practice of Urine Precipitation Test), K. K. Kindai Shuppan, Nov. 30, 1996, 2 pages.

* cited by examiner

*Primary Examiner*—Jon Weber
*Assistant Examiner*—Paul Martin
(74) *Attorney, Agent, or Firm*—Oblon, Spivak, McClelland, Maier & Neustadt, P.C.

(57) ABSTRACT

A microorganism staining agent characterized in that an alkali substance and a diazo dye or xanthene dye are contained therein; and a method of detecting microorganisms with the use of the agent. There are provided a microorganism staining agent which resolves the problem of pretreatment posed by the conventional direct speculum method, being capable of staining microorganisms in shorter time; and a method of detecting microorganisms with the use of the agent.

22 Claims, 2 Drawing Sheets

MICROORGANISM STAINING AGENT AND USE THEREOF

TECHNICAL FIELD

The present invention relates to a microorganism staining agent, and more specifically, to a microorganism staining agent capable of staining microorganisms such as bacteria and fungus more rapidly than conventional methods and to a microorganism detection method using the microorganism staining agent.

BACKGROUND ART

Conventional methods for detecting microorganisms such as bacteria and fungus include a direct microscopic count method wherein a specimen is microscopically examined after being pretreated and a cultivation examination method wherein the specimen is examined after cultivating the microorganisms. The direct microscopic count method is often used at medical sites in particular due to convenience.

As known methods for pretreatment in the direct microscopic count method, a potassium hydroxide method, dimethylsulfoxide (DMSO)-potassium hydroxide method, and Parker ink-potassium hydroxide method can be given (Hideyo Yamaguchi et al., Report of the Standardization Committee of the Japanese Society for Medical Mycology, "Jpn. J. Med. Mycol.", 1995, Vol. 36, pp. 61-86).

Since the potassium hydroxide and DMSO-potassium hydroxide methods do not stain the microorganism, there are problems such as difficulty in detecting *Malassezia* and requirement of skill in the detection under a microscope. Although the microorganism are stained in the Parker ink-potassium hydroxide method, the method has a problem of requiring a long time for staining from several hours to overnight. There are also problems that the type of ink that can be used in this staining method is restricted. Since the ink itself is comprised of several components, stainability of the bacteria may change according to the composition of the ink.

Therefore, in order to overcome the problems during pretreatment in the conventional direct microscopic count method, an objective of the present invention is to provide a staining agent that can stain microorganisms rapidly and a microorganism staining and detection method using the same.

DISCLOSURE OF THE INVENTION

In view of these circumstances, the inventors have conducted extensive research to achieve the above objective and discovered that staining and detection of microorganisms can be accomplished rapidly using a staining agent comprising an alkali substance and a specific dye, thereby completing the present invention.

Specifically, the present invention provides a microorganism staining agent characterized by comprising an alkali substance and a diazo dye or xanthene dye.

The present invention also provides a microorganism detection method characterized by staining microorganisms by adding the staining agent to a specimen comprising microorganisms and detecting the stained microorganisms.

BEST MODE FOR CARRYING OUT THE INVENTION

Figure 1:
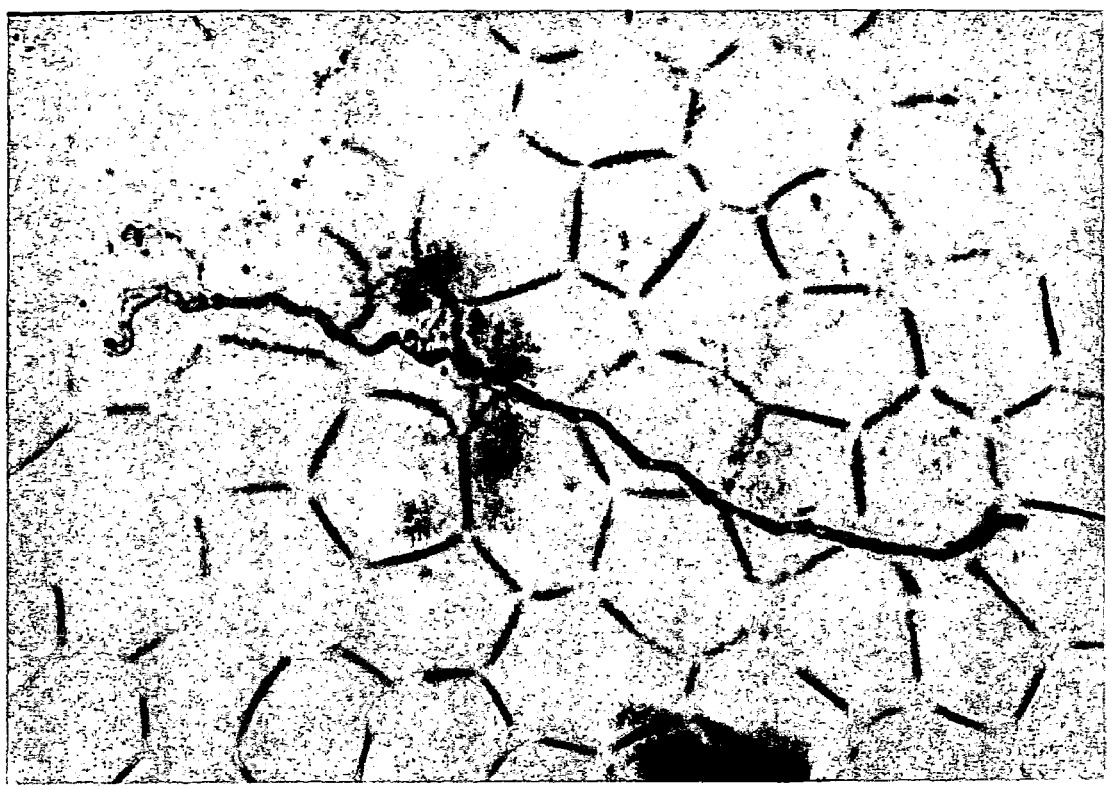
FIG. 1 shows a photomicrograph (×400) of staining conducted using the staining agent of Example 1.

The microorganism staining agent of the present invention (hereinafter referred to as "staining agent of the present invention") comprises an alkali substance and a diazo dye or xanthene dye.

As examples of the alkali substance used in the staining agent of the present invention, inorganic alkali such as potassium hydroxide, sodium hydroxide, barium hydroxide, potassium carbonate, sodium carbonate, ammonium carbonate, tripotassium phosphate, dipotassium hydrogen phosphate, trisodium phosphate, disodium hydrogen phosphate, and ammonia; organic alkali such as alkylamines such as methylamine, ethylamine, and isopropylamine, and alkanol amines such as methanolamine, ethanolamine, diethanolamine, triethanolamine, isopropanolamine, and diisopropanolamine; and the like can be given. Of these alkali substances, sodium hydroxide and potassium hydroxide are preferable, with potassium hydroxide being particularly preferable. The alkali substance is incorporated in the staining agent of the present invention in an amount of 10-40 mass % (hereinafter, simply referred to as "%") and preferably 15-30%.

As preferable examples of the diazo dye used in the staining agent of the present invention, Chicago Sky Blue 6B, Evans Blue, Direct Blue 15, Trypan Blue, Benzopurpurin 4B, Congo Red, and the like can be given with Chicago Sky Blue 6B being particularly preferable. The diazo dye is incorporated in the staining agent of the present invention in an amount of 0.01-2% and preferably 0.1-1%.

As preferable examples of the xanthene dye used in the staining agent of the present invention, Rhodamine B, Rhodamine B base, Rhodamine 123 hydrate, Rhodamine 6G, Rhodamine 110, Rhodamine 575, and the like can be given with Rhodamine B being particularly preferable. The xanthene dye is incorporated in the staining agent of the present invention in an amount of 0.001-1% and preferably 0.005-0.5%.

In addition to the above components, the staining agent of the present invention may comprise methanol and/or dimethyl sulfoxide. The methanol is preferably incorporated in the staining agent of the present invention in an amount of 0-30% with 0-20% being particularly preferable. The dimethyl sulfoxide is preferably incorporated in the staining agent of the present invention in an amount of 0-20% with 0-10% being particularly preferable.

Since the addition of the methanol and/or dimethyl sulfoxide can control stainability of the cell without affecting the stainability of the microorganism, the staining agent comprising methanol and/or dimethyl sulfoxide distinctly stains the microorganism thereby allowing easy detection thereof. In addition, methanol and/or dimethyl sulfoxide are particularly effective when used with the diazo and xanthene dyes having a low solubility in an alkali solution such as Rhodamine B since the methanol and/or dimethyl sulfoxide can increase solubility of these dyes.

In the manufacture of the staining agent of the present invention, the alkali substance is dissolved in water to obtain an alkali solution and the diazo dye or xanthene dye and, when necessary, methanol and/or dimethyl sulfoxide are added to the solution and mixed. The dye having a low solubility in an alkali solution is dissolved in one or more types of methanol or dimethyl sulfoxide beforehand and then mixed with the alkali solution.

The staining agent of the present invention obtained in this manner can be used for staining cutaneous fungi such as *Trichophyton*, fungi such as *Candida, Malassezia*, and the like, and bacteria such as Gram-positive bacteria, Gram-negative bacteria, and the like.

The method for detecting microorganisms using the staining agent of the present invention will now be described.

In order to detect microorganisms using the staining agent of the present invention, the microorganisms are stained by applying the staining agent of the present invention to a sample taken from an area where the microorganisms are believed to be present and the sample is allowed to stand for about 20-30 minutes. Various types of samples can be used in accordance with the area of extraction. For example, when *Trichophyton* in the foot or hair is to be detected, samples are taken from the keratin of dander, vesicle, vesicle coat, papula, and the like, when *Trichophyton* in the nails is to be detected, samples are taken from the substratum of the nail plate, the nail bed, and the like, and when sycosis or kerion is to be detected, diseased hair that can be easily removed from a lesion is used as a sample. The staining agent of the present invention is usually applied to the sample in an amount of about several drops.

Since the staining agent of the present invention has high heat stability, the specimen can be heated at 60-80° C. for about 2-5 minutes using a fixed temperature hot plate or the like after applying the staining agent of the present invention to the specimen in order to stain the microorganism in a short period of time.

The specimen to which the staining agent of the present invention was applied is, for example, placed on a slide glass, and covered with a cover glass, and the top of the cover glass is lightly pressed with a glass rod or the like in order to thinly spread the sample. The presence of staining in the sample is then observed using a microscope or the like at a 100-200× magnification.

After confirming the presence of staining, the sample is further examined using a microscope at a 400× magnification to detect the presence of cutaneous fungi and fungi such as *Candida, Malassezia*, and the like in the sample by observing the parasitic form of these microorganisms. The presence of bacteria such as Gram-positive and Gram-negative bacteria can be determined by observing the sample at a 1000× magnification.

When a diazo dye is used in the staining agent of the present invention, the staining agent particularly preferably comprises 15-30% of the alkali substance, 0.1-1% of the diazo dye, 0-20% of methanol, and 0-2% of dimethylsulfoxide. When a xanthene dye is used in the staining agent of the present invention, the staining agent particularly preferably comprises 15-30% of the alkali substance, 0.005-0.5% of the xanthene dye, 0-30% of methanol, and 5-20% of dimethylsulfoxide.

By using the staining agent of the present invention as described above, the microorganisms can be stained in a shorter period of time and detected more correctly as compared with conventional microorganism staining-detection methods.

EXAMPLES

The present invention will now be described in detail by way of examples, which should not be construed as limiting the present invention.

Example 1

Staining Agent (1)

Chicago Sky Blue 6B (manufactured by Kanto Chemical Co., Inc.) was added to a 20% potassium hydroxide solution at a concentration of 0.5%, mixed, and dissolved to obtain a staining agent.

Example 2

Bacteria Staining and Detection in a Fungus Infected Area (1)

Lesion tissue (dander) extracted from an area suspected of being infected with epidermomycosis was used as a sample. The sample was placed on a slide glass, the staining agent of Example 1 was dropped onto the sample, and the sample was allowed to stand at room temperature for 20-30 minutes in order to soften the sample. After the sample was sufficiently softened, a cover glass was placed on the sample, the top of the cover glass was lightly pressed with a glass rod or the like to thinly spread out the sample, and the sample was observed using an optical microscope.

Results of observation at a 100-200× magnification confirmed the presence of stained (blue) microorganisms. Further observation at a 400× magnification confirmed the presence of cutaneous fungus and a parasitic form of *Candida* and *Malassezia*. FIG. 1 shows a photomicrograph at a 400× magnification.

Example 3

Bacteria Staining and Detection in a Fungus Infected Area (2)

Staining and microscopic observation was conducted in the same manner as Example 2 except for heating the sample at 60-80° C. for 2-5 minutes using a fixed temperature hot plate instead of allowing the sample to stand at room temperature.

Results of observation at a 100-200× magnification confirmed the presence of stained (blue) microorganisms. Further observation at a 400× magnification confirmed the presence of cutaneous fungus and a parasitic form of *Candida* and *Malassezia*. This confirms that heating causes the staining agent of the present invention to stain in a shorter period of time.

Example 4

The Effect of Methanol and Dimethyl Sulfoxide on the Detection of Microorganisms (1)

The following staining agents were prepared comprising Chicago Sky Blue 6B and KOH at fixed concentrations of 0.5% and 20%, respectively, and various concentrations of methanol (MeOH) and dimethyl sulfoxide (DMSO). The degree of sample cell staining and microorganism staining were evaluated based on the following criteria. The characteristics of the staining agents were collectively evaluated. The results are shown in Table 1.

(Concentration of MeOH and DMSO in the Staining Agent)
  Staining agent A: MeOH 0%/DMSO 0%
  Staining agent B: MeOH 10%/DMSO 0%
  Staining agent C: MeOH 20%/DMSO 0%
  Staining agent D: MeOH 30%/DMSO 0%
  Staining agent E: MeOH 40%/DMSO 0%
  Staining agent F: MeOH 0%/DMSO 1%
  Staining agent G: MeOH 10%/DMSO 1%
  Staining agent H: MeOH 20%/DMSO 1%
  Staining agent I: MeOH 0%/DMSO 2.5%
  Staining agent J: MeOH 10%/DMSO 2.5%
  Staining agent K: MeOH 20%/DMSO 2.5%

Evaluation Criteria:

Degree of Staining of Sample Cell
  Grade: Evaluation results
    +++: Dyed very darkly
    ++: Dyed darkly
      +: Dyed to some degree
      ±: Dyed lightly
      −: Did not dye Degree of Staining of Microorganism
  Grade: Evaluation results
    +++: Dyed very darkly
    ++: Dyed darkly
      +: Dyed to some degree
      ±: Dyed lightly
      −: Did not dye Overall Evaluation
  Grade: Evaluation results
    ⊚: High practical applicability as a staining agent
    ○: Can be used as a staining agent
    Δ: Can be used as a staining agent only with problems
    X: Cannot be used as a staining agent (Results)

TABLE 1

| Staining agent | Degree of staining | | Overall evaluation |
| --- | --- | --- | --- |
| | Sample cell | Microorganism | |
| Staining agent A | ± to ++ | + to +++ | ⊚ |
| Staining agent B | − to + | ++ to +++ | ⊚ |
| Staining agent C | − to + | +++ | ⊚ |
| Staining agent D | ± to ++ | ++ to +++ | ○ |
| Staining agent E | ± to ++ | + to ++ | Δ |
| Staining agent F | − | + to ++ | ○ |
| Staining agent G | ± | ++ | ⊚ |
| Staining agent H | − to ± | ++ to +++ | ⊚ |
| Staining agent I | − | + to ++ | ○ to Δ |
| Staining agent J | ± | + to ++ | ○ |
| Staining agent K | − | ++ | ○ |

Example 5

Staining Agent (2)

Chicago Sky Blue 6B and methanol were added to a 20% sodium hydroxide solution at a concentration of 0.5% and 20%, respectively, mixed, and dissolved to obtain a staining agent.

Example 6

Staining Agent (3)

5 mg of Rhodamine B (manufactured by Aldrich) was mixed with 1 ml of dimethyl sulfoxide to form a solution. 4 ml of water was added to this solution. This solution was mixed and dissolved with a 40% potassium hydroxide solution at a ratio of 1:1 to obtain a staining agent.

Example 7

Microorganism Staining and Detection in a Fungus Infected Area (3)

Figure 2:
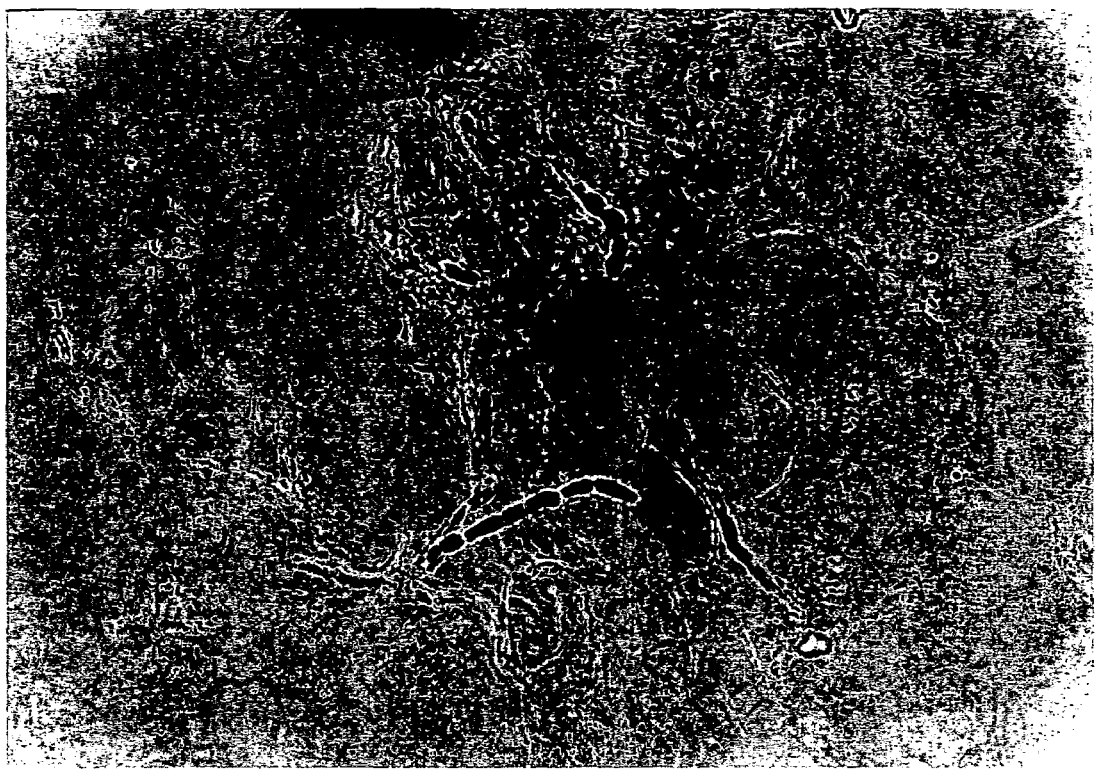
FIG. 2 shows a photomicrograph (×400) of staining conducted using the staining agent of Example 7.

Staining and microscopic observation was conducted in the same manner as in Example 2 except for using the staining agent of Example 6. FIG. 2 shows a photomicrograph at a 400× magnification.

Results of observation at a 100-200× magnification confirmed the presence of staining (red), whereby the presence of bacteria was detected. Cutaneous fungus and a parasitic form of *Candida* and *Malassezia* were observed at an increased magnification of 400×. FIG. 2 shows a photomicrograph at a 400× magnification.

Example 8

The Effect of Methanol and Dimethyl Sulfoxide on the Detection of Microorganisms (2)

The staining agents comprising Rhodamine B and KOH at fixed concentrations of 0.05% and 20%, respectively, and various concentrations of methanol (MeOH) and dimethyl sulfoxide (DMSO) as listed below were prepared. The degree of sample cell staining and microorganism staining were evaluated based on the criteria of Example 4. The overall characteristics of the staining agents were evaluated. The results are shown in Table 2.

(Concentration of MeOH and DMSO in the Staining Agent)
  Staining agent L: MeOH 10%/DMSO 0%
  Staining agent M: MeOH 25%/DMSO 0%
  Staining agent N: MeOH 0%/DMSO 10%
  Staining agent O: MeOH 10%/DMSO 10%
  Staining agent P: MeOH 20%/DMSO 10%
  Staining agent Q: MeOH 30%/DMSO 10%
  Staining agent R: MeOH 40%/DMSO 10%
  Staining agent S: MeOH 0%/DMSO 25%

(Results)

TABLE 2

| Staining agent | Degree of staining | | Overall evaluation |
| --- | --- | --- | --- |
| | Sample cell | Microorganism | |
| Staining agent L | ++ | ++ | X to Δ |
| Staining agent M | +++ | + | X |
| Staining agent N | ± to + | +++ | ⊚ |
| Staining agent O | ± to + | +++ | ⊚ |
| Staining agent P | + to ++ | ++ to +++ | ○ |
| Staining agent Q | ± | ++ | ○ |
| Staining agent R | − | + | Δ |
| Staining agent S | − | + | Δ |

Example 9

Staining Agent (4)

5 mg of Rhodamine B was mixed with 1 ml of dimethyl sulfoxide to form a solution. 4 ml of water was added to the solution. This solution was mixed and dissolved with a 40% sodium hydroxide solution at a ratio of 1:1 to obtain a staining agent.

Comparative Example 1

Comparative Staining Agent (1)

Aniline Blue (manufactured by Wako Pure Chemical Industries, Ltd.) was added to a 20% potassium hydroxide solution at a concentration of 1%, mixed, and dissolved to obtain a comparative staining agent. Staining and microscopic observation was conducted in the same manner as in Example 2 using this staining agent. However, staining could not be confirmed and microorganisms were not detected.

Comparative Example 2

Comparative Staining Agent (2)

Brilliant Blue R (manufactured by Sigma) and dimethyl sulfoxide were added to a 20% potassium hydroxide solution at a concentration of 0.5% and 10%, respectively, mixed, and dissolved to obtain a staining agent. Staining and microscopic observation was conducted in the same manner as in Example 2 using this staining agent. However, staining could not be confirmed and microorganisms were not detected.

Comparative Example 3

Comparative Staining Agent (3)

A cartridge of blue-black Platinum spare ink (manufactured by Platinum Pen Co., Ltd.) was mixed and dissolved with a 40% sodium hydroxide solution at a ratio of 1:1 to obtain a comparative staining agent. Staining and microscopic observation was conducted in the same manner as in Example 2 using this staining agent. However, staining could not be confirmed and microorganisms were not detected.

Comparative Example 4

Comparative Staining Agent (4)

A blue-black Uni-Ball Shigno UMR-85N replacement ink cartridge (manufactured by Mitsubishi Pencil Co., Ltd.) was mixed and dissolved with a 40% sodium hydroxide solution at a ratio of 1:1 to obtain a comparative staining agent. Staining and microscopic observation was conducted in the same manner as in Example 2 using this staining agent. However, staining could not be confirmed and microorganisms were not detected.

INDUSTRIAL APPLICABILITY

The staining agent of the present invention can be used in rapid staining and detection of microorganisms such as fungus and bacteria. The staining agent of the present invention has high storage stability and heat stability, thereby not causing problems such as reduction in stainability resulting from storage over a long period of time and heating during staining.

Therefore, the staining agent of the present invention is very effective in the staining of microorganisms such as fungus and bacteria.

The invention claime is:

1. A composition for staining a microorganism comprising:
   15 to 30 wt. % of an alkali substance; and
   Chicago Sky Blue 6B.

2. The composition according to claim 1, further comprising:
   0 to 20 wt. % of methanol; and
   0 to 2 wt. % of dimethyl sulfoxide, and
   wherein the amount of said Chicago Sky Blue 6B ranges from 0.1 to 1 wt. %.

3. The composition according to claim 2, wherein the amount of said methanol ranges from 10 to 20 wt. %.

4. The composition according to claim 2, wherein the amount of said dimethyl sulfoxide ranges from 1 to 2 wt. %.

5. The composition according to claim 1, wherein said microorganism is fungi.

6. The composition according to claim 5, wherein said fungi is a member of a genus selected from the group consisting of *Trichophyton*, *Candida* and *Malassezia*.

7. A method for detecting a microorganism in a sample comprising:
   contacting said microorganism with the composition of claim 1 to yield a stained microorganism; and
   detecting said stained microorganism by direct microscopy.

8. The method according to claim 7, further comprising:
   heating said sample to a temperature ranging from 60° C. to 80° C. for a period ranging from 2 minutes to 5 minutes after said contacting, but before said detecting.

9. The method according to claim 7, wherein said sample is obtained from a foot, a nail plate, a nail bed, a hair, a dander, a vesicle, and a papula.

10. The method according to claim 7, wherein said microorganism is fungi.

11. The method according to claim 10, wherein said fungi is a member of a genus selected from the group consisting of *Trichophyton*, *Candida* and *Malassezia*.

12. A composition for staining a microorganism comprising:
    15 to 30 wt. % of an alkali substance; and
    Rhodamine B.

13. The composition according to claim 12, further comprising:
    0 to 30 wt. % of methanol; and
    5 to 20 wt. % of dimethyl sulfoxide, and
    wherein the amount of said Rhodamine B ranges from 0.005 to 0.5 wt. %.

14. The composition according to claim 13, wherein the amount of said methanol ranges from 10 to 30 wt. %.

15. The composition according to claim 13, wherein the amount of said dimethyl sulfoxide ranges from 10 to 20 wt. %.

16. The composition according to claim 12, wherein said microorganism is fungi.

17. The composition according to claim 16, wherein said fungi is a member of a genus selected from the group consisting of *Trichophyton*, *Candida* and *Malassezia*.

18. A method for detecting a microorganism in a sample comprising:
    contacting said microorganism with the composition of claim 12 to yield a stained microorganism; and
    detecting said stained microorganism by direct microscopy.

19. The method according to claim 18, further comprising:
    heating said sample to a temperature ranging from 60° C. to 80° C. for a period ranging from 2 minutes to 5 minutes after said contacting, but before said detecting.

20. The method according to claim 18, wherein said sample is obtained from a foot, a nail plate, a nail bed, a hair, a dander, a vesicle, and a papula.

21. The method according to claim 18, wherein said microorganism is fungi.

22. The method according to claim 21, wherein said fungi is a member of a genus selected from the group consisting of *Trichophyton*, *Candida* and *Malassezia*.

* * * * *